(12) United States Patent
Mestha et al.

(10) Patent No.: US 9,693,710 B2
(45) Date of Patent: Jul. 4, 2017

(54) SYSTEM AND METHOD FOR DETERMINING RESPIRATION RATE FROM A VIDEO

(71) Applicant: Xerox Corporation, Norwalk, CT (US)

(72) Inventors: Lalit Keshav Mestha, Fairport, NY (US); Beilei Xu, Penfield, NY (US); Survi Kyal, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 464 days.

(21) Appl. No.: 14/519,641

(22) Filed: Oct. 21, 2014

(65) Prior Publication Data

US 2016/0106340 A1    Apr. 21, 2016

(51) Int. Cl.
*A61B 6/00* (2006.01)
*A61B 5/08* (2006.01)
*A61B 5/00* (2006.01)
*A61B 5/11* (2006.01)

(52) U.S. Cl.
CPC .......... *A61B 5/0816* (2013.01); *A61B 5/1128* (2013.01); *A61B 5/7282* (2013.01); *A61B 5/746* (2013.01); *A61B 5/7485* (2013.01); *A61B 2576/00* (2013.01)

(58) Field of Classification Search
CPC ..... A61B 5/746; A61B 5/1128; A61B 5/0816; A61B 5/7282

USPC ......................................................... 600/476
See application file for complete search history.

(56) References Cited

U.S. PATENT DOCUMENTS

| | | |
|---|---|---|
| 8,792,969 B2 | 7/2014 | Bernal et al. |
| 2013/0324875 A1 | 12/2013 | Bernal et al. |
| 2013/0324876 A1 | 12/2013 | Bernal et al. |

*Primary Examiner* — Amanda Patton
*Assistant Examiner* — Philip C Edwards
(74) *Attorney, Agent, or Firm* — Philip E. Blair; Fleit Gibbons Gutman; Bongini & Bianco P.L.

(57) ABSTRACT

What is disclosed is a system and method for determining respiration rate from a video of a subject. In one embodiment, a video is received comprising plurality of time-sequential image frames of a region of a subject's body. Features of pixels are extracted from that region from each image frame and vectors formed from these features. Each image frame has an associated feature vector. A N×M video matrix of the vectors of length N is constructed such that a total number of columns M in the video matrix correspond to a time duration over which the subject's respiration rate is to be determined. The video matrix is processed to obtain a matrix of eigenvectors where principal axes of variations due to motion associated with respiration are contained in a first few eigenvectors. One eigenvector is selected from the first few eigenvectors. A respiration rate is obtained from the selected eigenvector.

31 Claims, 6 Drawing Sheets

US 9,693,710 B2

SYSTEM AND METHOD FOR DETERMINING RESPIRATION RATE FROM A VIDEO

TECHNICAL FIELD

The present invention is directed to systems and methods for determining respiration rate from a video of a subject being monitored for respiratory function.

BACKGROUND

Monitoring patient respiration rate is of clinical importance in the early detection of potentially fatal respiratory events such as acute respiratory failure and pulmonary diseases. Current technologies require that the resting patient wear sensing devices across their chest (e.g., chest belt) so that respiratory measurements can be estimated. Such a requirement can lead to discomfort, psychological dependence, and loss of dignity. Elderly patients and those suffering from chronic conditions are even more likely to suffer from such negative effects of monitoring. The present invention is specifically directed to this effort.

INCORPORATED REFERENCES

The following U.S. Patents, U.S. Patent Applications, and Publications are incorporated herein in their entirety by reference.

"Processing A Video For Tidal Chest Volume Estimation", U.S. patent application Ser. No. 13/486,637, by Bernal et al.

"Processing A Video For Respiration Rate Estimation", U.S. patent application Ser. No. 13/529,648, by Bernal et al.

"Respiratory Function Estimation From A 2D Monocular Video", U.S. patent application Ser. No. 13/680,838, by Bernal et al.

BRIEF SUMMARY

What is disclosed is a system and method for determining respiration rate from a video of a subject being monitored for respiratory function. One embodiment of the present method involves the following. First, a video of a subject is received. The video comprises a plurality of time-sequential image frames of a region of interest of the subject's body where a signal corresponding to respiration can be registered by at least one imaging channel of a video imaging device. Features of pixels are then extracted from the region of interest from each image frame and vectors are formed from the extracted features. Each image frame has an associated feature vector. Feature vectors can comprise, for instance, an intensity component, a location component, or a motion component. Thereafter, a N×M video matrix of the sequentially successive feature vectors of length N is constructed wherein a total number of columns M in the video matrix corresponds to a time duration over which a respiration rate for the subject is to be determined. The video matrix is processed to obtain a matrix of eigenvectors wherein the matrix of eigenvectors comprises orthonormal vectors obtained by computing mean and covariance matrices using singular value decomposition. The eigenvector matrix is such that principal axes of variations due to motion associated with the subject's respiration are contained in a first few eigenvectors. One of the first few eigenvectors is selected and the subject's respiration rate is then extracted from the selected eigenvector. In one embodiment hereof, extracting the respiration rate from the selected eigenvector involves generating a power spectral density curve for the selected eigenvector and identifying a frequency within the power spectral density curve with the highest signal strength. The identified frequency is the subject's respiration rate. The subject's respiration rate is then communicated to a display device. If the subject's respiration rate is not within a normal range, an alert can be initiated and/or a medical professional can be signaled. The present method can be processed in real-time from a streaming video of the subject such that respiration rate can be determined on a continuous basis.

Features and advantages of the above-described method will become apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for determining respiration rate from a video of a subject being monitored for respiratory function.

Non-Limiting Definitions

A "subject" refers to a living being which is being monitored for respiration rate determination. Although the term "person" or "patient" may be used throughout this disclosure, it should be appreciated that the subject may be something other than a human such as, for example, a primate. Therefore, the use of such terms is not to be viewed as limiting the scope of the appended claims strictly to humans.

A "video", as is generally understood, is to a time-varying sequence of image frames captured of one or more regions of interest of a subject where a signal corresponding to respiration can be registered by at least one imaging channel of a video imaging device used to capture that video. It should be appreciated that the video may also contain other components such as, audio, time reference signals, frame rate, and the like. The video is captured by a video imaging device.

A "video imaging device" refers to a single-channel or multi-channel video camera for acquiring a video. Video imaging devices include color (RGB) video cameras. A video imaging device may have a plurality of outputs from which the video can be retrieved or otherwise received on a per-channel basis and may incorporate one or more memory, storage devices, and processors for executing machine readable program instructions for processing and analyzing video in accordance with the teachings hereof. Video captured by a video imaging device is processed to isolate one or more regions of interest.

Figure 1:
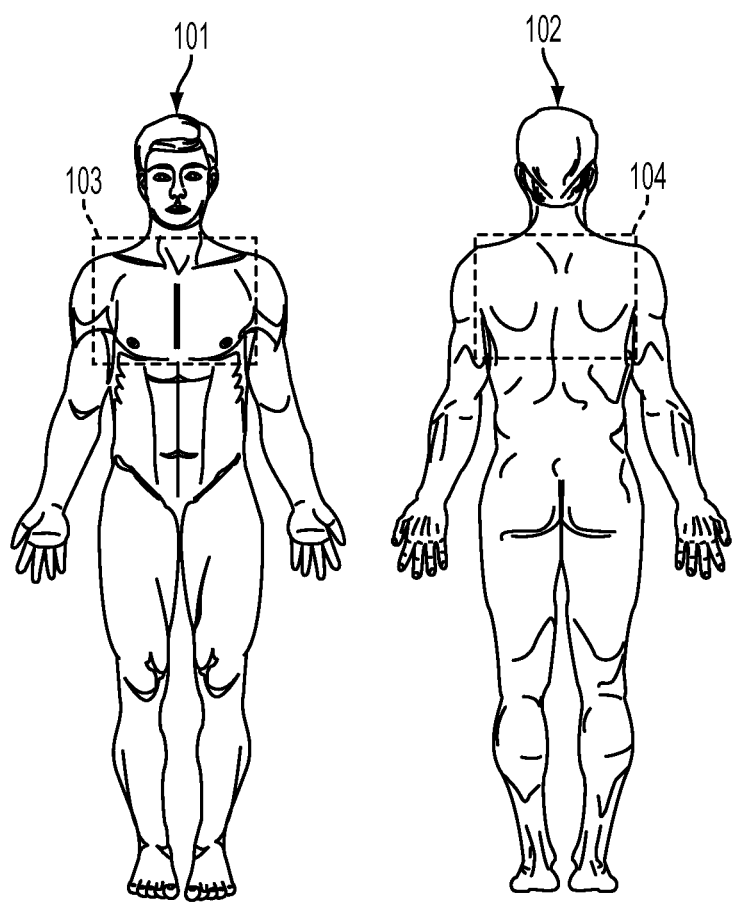
FIG. 1 shows both an anterior (frontal) view and a posterior (rear) view of an adult human.

A "region of interest" of a subject refers to at least a partial view of a region of the subject's body (as seen through the aperture of the video imaging device) where a respiratory signal can be registered by at least one imaging channel of the video imaging device. Such regions are those which move due to an expansion and contraction of the chest during respiration. Body regions include the anterior thoracic region, a side view of the thoracic region, a back region of the dorsal body and a facial region. FIG. 1 shows an anterior (frontal) view 101 of an adult human as well as a posterior (rear) view 102. In the embodiment of FIG. 1, regions of interest 103 and 104 outline the subject's anterior thoracic region and the posterior thoracic region, respectively, where respiratory signals can be acquired by a video imaging device. The region of interest may be covered with a sheet or an article of clothing. Regions of interest are isolated in the video image frames for processing.

"Isolating a region of interest" can be effectuated in a variety of ways using any of a wide array of techniques that are well established in the image processing arts. Pixels can be isolated in the image frames using image processing techniques such as pixel classification based on color, texture, spatial features, spectral information, object identification such as face or thoracic region recognition, pattern recognition, and motion detection. Pixels associated with regions of interest can also be identified in image frames for processing by a user selection. For example, during system setup and configuration, a technician may use a mouse or a touchscreen display to manually draw a rubber-band box around one or more areas of a displayed video of the subject thereby defining the one or more regions of interest with a boundary thereof being stored and used to isolate these regions. Features are obtained from the pixels in the isolated regions of interest.

A "feature vector" contains features obtained from processing pixels in the isolated region(s) of interest. Features comprising a feature vector include pixel intensity values, pixel location in the image frame, and one or more motion components such as amount of pixel movement between adjacent frames. If the video imaging device used to capture the video of the subject is a color video camera with red, green and blue (RGB) channels, intensity components comprising the feature vector can be obtained from any or a combination of the imaging channels on a per-pixel basis. Pixels in one or more regions of interest may be grouped according to features and their mean values or higher order statistics computed. Intensity components can also be an algebraic sum of pixel values from each of the RGB channels in a given region of interest. Pixels may be spatially filtered to reduce noise. Temporally sequential feature vectors of length N are used to construct a N×M matrix with a total of M columns in the video matrix corresponding to a time duration and video frame rate over which a respiration rate for the subject is to be determined. The N×M video matrix is processed to obtain a matrix of eigenvectors.

An "eigenvector" (from the German word eigen for "unique to" or "peculiar to") are a special set of vectors associated with a linear system of equations (i.e., a matrix equation) that are sometimes also known as characteristic vectors, proper vectors, or latent vectors. The determination of the eigenvectors and eigenvalues of a system is extremely important in physics and engineering, where it is equivalent to matrix diagonalization and arises in such common applications as stability analysis, the physics of rotating bodies, and small oscillations of vibrating systems, to name only a few. Each eigenvector is paired with a corresponding so-called eigenvalue. The decomposition of a square matrix A into eigenvalues and eigenvectors is known in this work as eigen decomposition, and the fact that this decomposition is always possible as long as the matrix A is square is known as the eigen decomposition theorem. The eigenvector of a square matrix A is a non-zero vector $v$ that, when the matrix multiplies $v$, yields a constant multiple of $v$, the latter multiplier being commonly denoted by $\lambda$ where $Av=\lambda v$. The number $\lambda$ is often referred to as the eigenvalue of A corresponding to $v$. The set of all eigenvectors of a matrix (or linear operator), each paired with its corresponding eigenvalue, is called the eigensystem of that matrix. Any multiple of an eigenvector is also an eigenvector, with the same eigenvalue. An eigenspace of a matrix is the set of all eigenvectors with the same eigenvalue, together with the zero vector. An eigenbasis for a matrix is any basis for the set of all vectors that consists of linearly independent eigenvectors of that matrix. Not every matrix has an eigenbasis. Mathematically, there are left eigenvectors and right eigenvectors. However, for many problems, it is sufficient to consider only right eigenvectors. Thus, the term eigenvector without a "left" or "right" qualification is generally understood to mean a right eigenvector. The reader is directed to: "*Eigenvalues of Matrices*", Françoise Chatelin, Society for Industrial and Applied Mathematics, (2012), ISBN-13: 978-1611972450 and "*Mathematical Methods for Physicists, Seventh Edition: A Comprehensive Guide*", George B. Arfken, Hans J. Weber, Academic Press, $7^{th}$ Ed. (2012), ISBN-13: 978-0123846549, both of which are incorporated herein in their entirety by reference.

A "matrix of eigenvectors", as used herein, is a matrix of orthonormal eigenvectors obtained by computing a derivative of the video matrix, computing a mean and a covariance matrix using singular value decomposition, taking an L2 norm of each row vector, and retaining all feature points with an L2 norm that is below a pre-defined maximum value. The resulting matrix is such that principal axes of variations due to motion associated with the subject's respiration are contained in a first few eigenvectors. In accordance with the teachings hereof, one of the first few eigenvectors is selected.

"Selecting one of a first few eigenvectors" means to either manually or automatically identify or otherwise obtain at least one eigenvector from the matrix of top-most (or dominant) eigenvectors for respiration rate determination. A manual selection involves, for example, a user making a selection from a touchscreen where at least the top-most eigenvectors are displayed. The user can pick one of the vectors for respiration determination. In another embodiment, a first eigenvector in the matrix of eigenvectors is automatically selected for respiration determination when the user recognizes that the respiration related motion is the leading cause for the variations observed in the eigenvector. In yet another embodiment, a second or third eigenvector in the matrix of eigenvectors is selected or otherwise identified for processing for respiration rate determination. It should be understood that the ordering in the matrix of eigenvectors (or a transpose thereof) is from top to bottom with the top-most eigenvector being a first eigenvector in the matrix and the bottom-most eigenvector being a last eigenvector in the matrix.

"Extracting respiration rate from the selected eigenvector" can be effectuated by generating a power spectral density curve for the selected eigenvector and identifying a frequency within the power spectral density curve with highest signal strength. The identified frequency comprises the subject's respiration rate.

"Respiration rate" is often measured when a subject is at rest and simply involves counting the number of breaths taken in a minute. A resting adult human takes about 12-20 breaths per minute depending on the overall condition of the cardio-vascular and respiratory systems. The respiratory rate can be utilized to determine various aspects of the subject's respiratory function. Restrictive pulmonary diseases such as pulmonary fibrosis, pneumothorax, and Infant Respiratory Distress Syndrome, decrease lung volume, whereas obstructive pulmonary diseases such as asthma, bronchitis, and emphysema, obstruct airflow increase.

Figure 2:
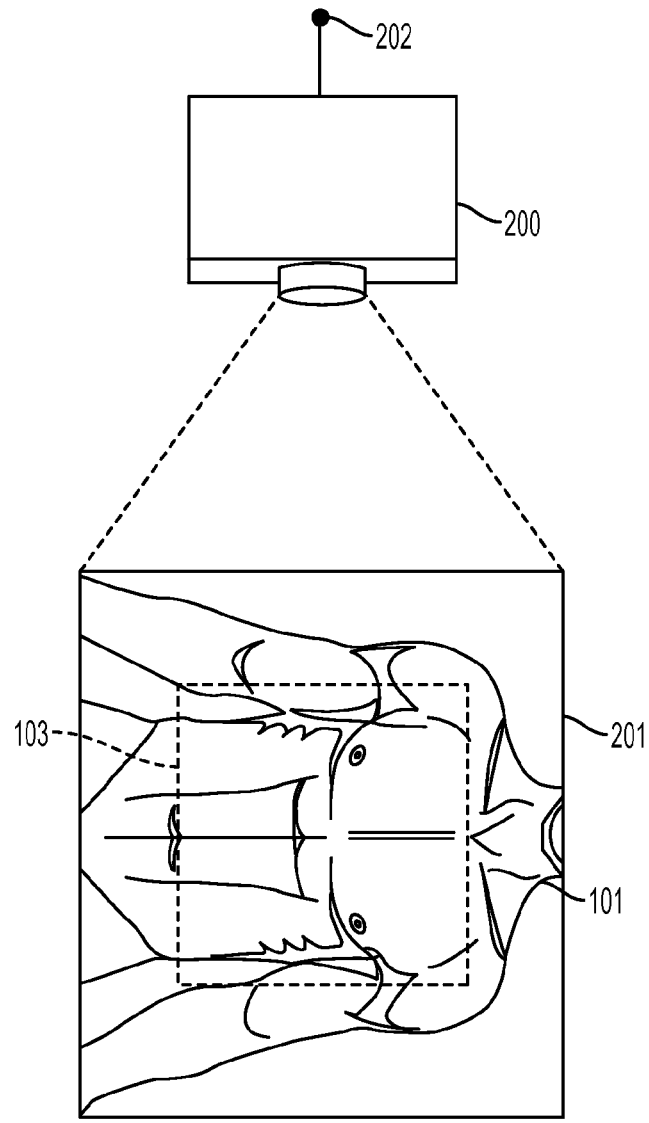
FIG. 2 shows a video imaging device capturing image frames of a region of interest of the subject of FIG. 1.

"Receiving a video" is intended to be widely construed and includes retrieving, capturing, acquiring, or otherwise obtaining video image frames for processing in accordance with the methods disclosed herein. FIG. 2 shows a video imaging device 200 capturing image frames (collectively at 201) of a region of interest 103 of the subject 101 of FIG. 1. The video imaging device is shown having a communication element 202 which effectuates a bi-directional communication with a remote device over a wireless network, such as a computer workstation, where the video image frames are received for processing in accordance with the methods disclosed herein. The video imaging device may further comprise a video analysis module which performs the functionality of the present method. Video image frames can be retrieved from a memory or storage device of the video imaging device. The video can be received or retrieved from a remote device over a network, or from a media such as a CDROM or DVD. Image frames may be downloaded from a web-based system or application which makes video images available for processing in accordance with the methods disclosed herein. Video image frames can also be received from an application such as those which are available for handheld cellular devices and processed on the cellphone or other handheld computing device such as an iPad or tablet.

It should be appreciated that the steps of "extracting", "forming", "constructing", "selecting", "generating", "processing", and the like, include the application of various mathematical operations as applied to data and signals, according to any specific context or for any specific purpose. The terms in this Detailed Description and claims include any activity, in hardware or software, having the substantial effect of the mathematical or signal-processing action. It should be appreciated that such steps may be facilitated or otherwise effectuated by a microprocessor executing machine readable program instructions retrieved from a memory or storage device.

Flow Diagram of One Embodiment

Figure 3:
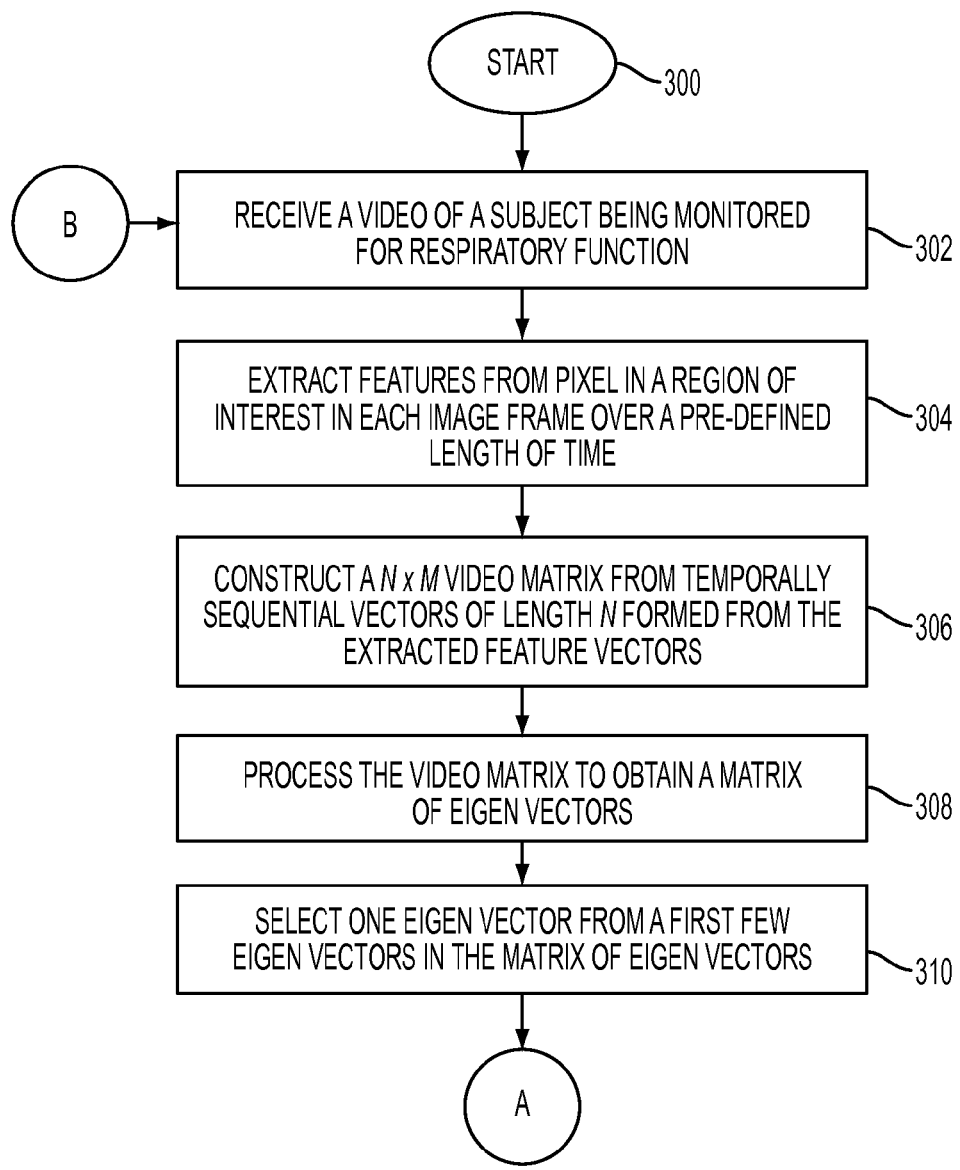
FIG. 3 is a flow diagram which illustrates one example embodiment of the present method for determining respiration rate from a video of a subject.

Reference is now being made to the flow diagram of FIG. 3 which illustrates one example embodiment of the present method for determining respiration rate from a video of a subject. Flow processing begins at step 300 and immediately proceeds to step 302.

At step 302, receive a video of a subject being monitored for respiratory function. The video comprises a plurality of time-sequential image frames of at least one region of interest of the subject's body where a signal corresponding to respiration can be registered by at least one imaging channel of a video imaging device. Example regions of interest are shown in FIG. 1.

At step 304, extract features of pixels in a region of interest in each image frame over a pre-defined period of time.

At step 306, construct a N×M video matrix from temporally sequential vectors of length N formed from the extracted feature vectors. The video matrix has a total number of columns M that corresponds to a time duration over which the subject's respiration rate is desired to be determined.

At step 308, process the video matrix to obtain a matrix of eigenvectors. The eigenvector matrix is such that principal axes of variations due to motion associated with the subject's respiration are contained in a first few eigenvectors.

At step 310, select one eigenvector from a first few eigenvectors in the matrix of eigenvectors. A selection can be made using, for example, the workstation of FIG. 5.

Figure 4:
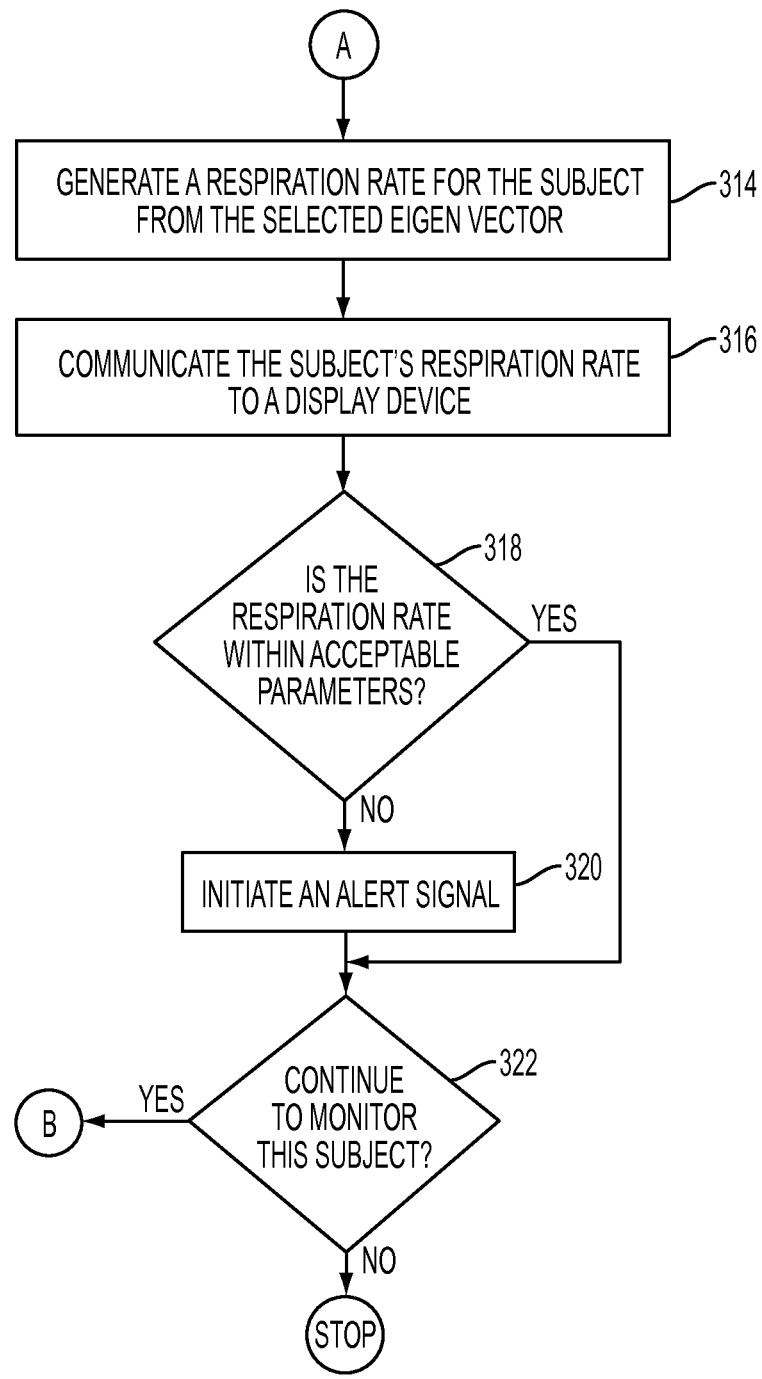
FIG. 4 is a continuation of the flow diagram of FIG. 3 with flow processing continuing with respect to node A.

Reference is now being made to the flow diagram of FIG. 4 which is a continuation of the flow diagram of FIG. 3 with flow processing continuing with respect to node A.

At step 312, generate a respiration rate for the subject from the selected eigenvector.

At step 314, communicate the subject's respiration rate to a display device. In other embodiments, the respiration rate is communicated to a memory, a storage device, a handheld wireless device, a handheld cellular device, and a remote device over a network.

At step 316, a determination is made whether the subject's respiration is within acceptable parameters as determined by a medical professional. If the subject's respiration rate is not within acceptable parameters then, at step 318, an alert signal is initiated. A signal may further be sent to a medical professional.

At step 320, a determination is made whether to continue to monitor this subject for respiratory function. If so then processing continues with respect to node B wherein, at step 302, more video of this subject is received. Processing repeats in a similar manner. Otherwise, in this embodiment, further processing stops.

It should be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Example Video Processing System

Figure 5:
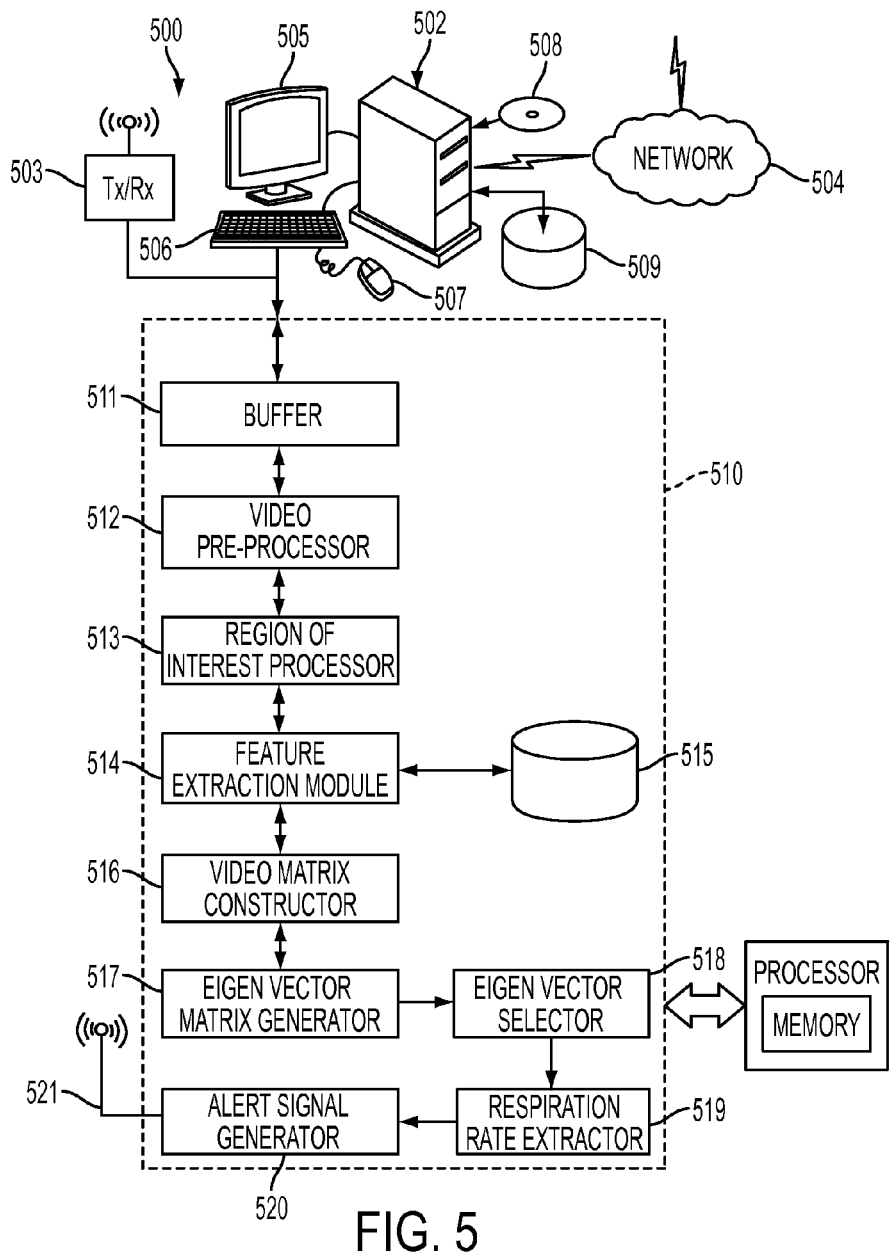
FIG. 5 illustrates a block diagram of one example video processing system for implementing various aspects of the present method as described with respect to the flow diagrams of FIGS. 3 and 4.

Reference is now being made to FIG. 5 which illustrates a block diagram of one example video processing system for implementing various aspects of the present method as described with respect to the flow diagrams of FIGS. 3 and 4.

Workstation 500 has a computer case 502 which houses various components such as a motherboard with a processor and memory, a network card, a video card, a hard drive capable of reading/writing to machine readable media 508 such as a floppy disk, optical disk, CD-ROM, DVD, magnetic tape, and the like, and other software and hardware needed to perform the functionality of a computer workstation. The workstation further includes a display device 505, such as a CRT, LCD, or touchscreen device, for displaying video, regions of interest, features, computed values, medical information, results, and the like, which are produced or are otherwise generated by any of the modules of FIG. 6. A user can view any of that information and make a selection from menu options displayed thereon. Keyboard 506 and mouse 507 effectuate a user input or selection as needed. The workstation 500 implements a database 509 wherein records are stored, manipulated, and retrieved in response to a query. Such records, in various embodiments, take the form of patient medical history stored in association with information identifying the patient along with medical information, patient respiratory function history, and the like. Although the database is shown as an external device, the database may be internal to the workstation mounted, for example, on a hard disk therein.

The workstation has an operating system and other specialized software configured to display alphanumeric values, menus, scroll bars, dials, slideable bars, pull-down options, selectable buttons, and the like, for entering, selecting, modifying, and accepting information needed for respiration rate determination in accordance with the methods disclosed herein. A user or technician may use the workstation to identify regions of interest in the image frames, grouping pixels, identifying features of interest, set various parameters, and/or use the workstation to facilitate the functionality of any of the modules and processing units of the Image Processing Unit 510. User input, default settings, and selections may be stored/retrieved in either of storage devices 508 and 509. Default settings and initial parameters can also be retrieved from any of these storage devices. A user may adjust various parameters being utilized or dynamically adjust settings in real-time. Any alert signals generated may be received and viewed by the workstation and/or communicated to one or more remote devices over network 504. Although shown as a desktop computer, it should be appreciated that the workstation can be a laptop, mainframe, or a special purpose computer such as an ASIC, circuit, or the like. The embodiment of the workstation is illustrative and may include other functionality known in the arts. Workstation 502 is in communication with Image Processing Unit 510 for processing the video in accordance with the teachings hereof.

Video Processing Unit 510 is shown comprising at least one buffer 511. Such a buffer may be used for queuing image frames and other information about the received image frames such as, for instance, one or more regions of interest within the image frames, size of the video, time/date information, and the like. The buffer may also be configured to store data, mathematical formulas and other representations to facilitate processing of the image in accordance with the teachings hereof. Video Pre-Processor 512 performs any pre-processing of the video as may be desired or required such as, for example, to compensate for non-uniform illumination due to a curvature of a surface of the skin, for motion induced blur due to body or surface motion, imaging blur, slow illuminant variation, and the like. Region of Interest Processor 513 receives the pre-processed image frames and proceeds to identify one or more regions of interest within each of the frames.

Feature Extraction Module 514 receives the identified region(s) of interest, on a per-frame basis, and extracts from those region(s) of interest features of pixels and forms vectors of length N from the extracted features. These feature vectors are then stored to storage device 515. Information to perform any of the functions of any of the modules may be retrieved from storage device 515 or may be received via a user input using the keyboard and mouse of workstation 500. Video Matrix Constructor 516 receives the extracted feature vectors and proceeds to construct a video matrix wherein a total number of columns M in the video matrix correspond to a time duration over which a respiration rate for the subject is to be determined. Eigenvector Matrix Generator 517 receives the video matrix and processes the video matrix to obtain a matrix of eigenvectors. The eigenvector matrix is such that principal axes of color variations due to motion associated with the subject's respiration are contained in a first few eigenvectors. Eigenvector Selector Module 518 facilitates a selection of one of the first few eigenvectors either manually or automatically. Such a selection may be made by a user or technician using the keyboard/mouse of the workstation 500. Respiration Rate Extractor 519 receives the selected eigenvector from Module 518 and proceeds to process the selected eigenvector to obtain a respiration rate for the subject.

Alert Signal Generator Module 520 receives the subject's respiration rate and determines whether the respiration rate is within acceptable limits as determined by a medical profession. If the respiration is not within acceptable limits then an alert signal is generated via a transmitter 521 shown as an antenna. Transmitter 521 may further communicate some or all of the original video to a third party such as, for example, a nurse or respiratory therapist. Transmitted data, images, respiration rate, compute values, features, and the like, may be communicated to the workstation through element 503 and displayed on the display device 505 for review and further processing.

Each of the modules and processing units of the system 510 is also in communication with workstation 500 via pathways not shown and may further be in communication with one or more remote devices over network 504. It should be appreciated that some or all of the functionality performed by any of the modules and processing units of system 510 may be performed, in whole or in part, by the workstation 500. Any of the modules may be placed in communication with storage device 515. Processor and Memory are shown generally to execute machine readable program instructions which facilitate the functionality of any of the modules and processing units of FIG. 5.

Performance Results

Figure 6:
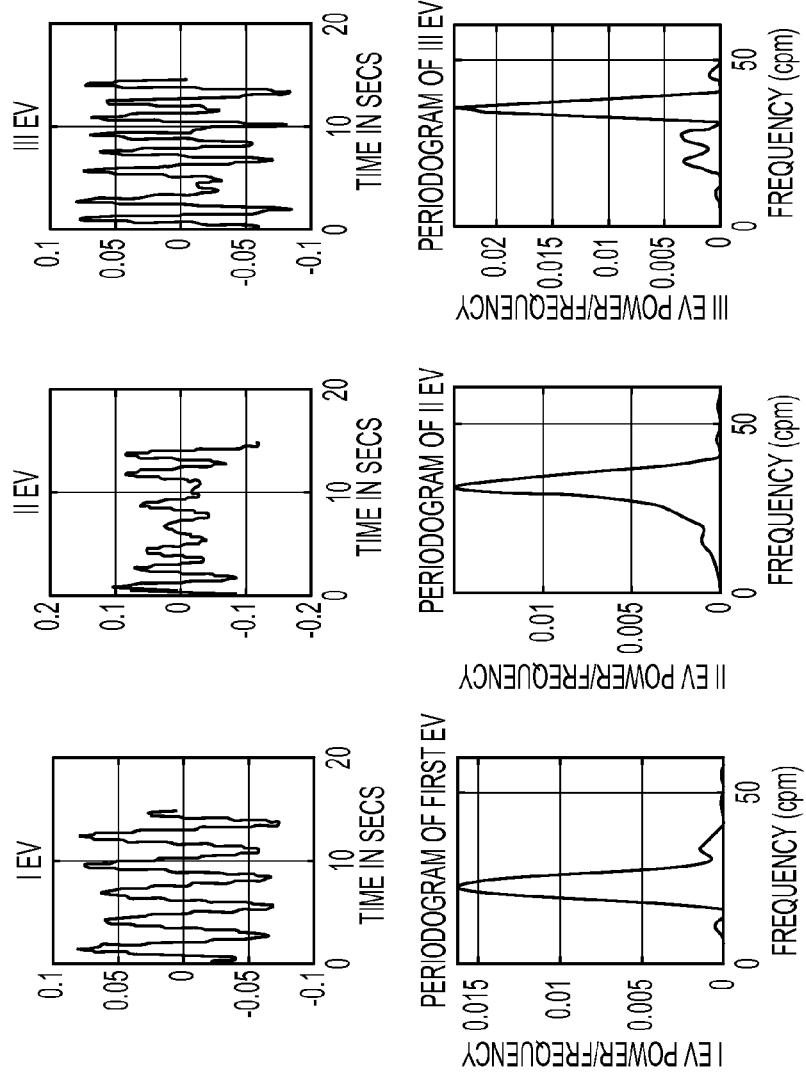
FIG. 6 shows the eigenvectors generated for each of three subjects and the resulting periodograms.

We have validated the method disclosed herein on two subjects and one simulated patient (SimMan). In all cases, a blue channel signal of the video imaging device was to show that this channel can also produce respiration rate. FIG. 6 shows the eigenvectors (top) generated for each of the three subjects and the resulting periodograms (bottom). The peak frequencies correspond, respectively, to 22 cpm, 32 cpm and 36 cpm when the actual respiration rate was 22 cpm.

Various Embodiments

Various modules of the embodiments hereof may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network. One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage device readable by a machine architecture or image processing system embodying executable program instructions capable of performing the methodology described in the flow diagrams.

Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining respiration rate from a video of a subject being monitored for respiratory function, the method comprising:
   receiving a video of a subject being monitored for respiratory function, said video comprising a plurality of time-sequential image frames of at least one region of interest of said subject's body where a signal corresponding to respiration can be registered by at least one imaging channel of a video imaging device;
   extracting, from said region of interest from said plurality of image frames, features of pixels and forming vectors of length N from said extracted features;
   constructing a N×M video matrix of temporally sequential feature vectors, a total number of columns M in said video matrix corresponding to a time duration over which a respiration rate for said subject is to be determined;
   processing said video matrix to obtain a matrix of eigenvectors, said eigenvector matrix being such that principal axes of variations due to motion associated with said subject's respiration are contained in a first few eigenvectors;
   selecting one eigenvector from said first few eigenvectors; and
   extracting a respiration rate for said subject from said selected eigenvector.

2. The method of claim 1, wherein said feature vector comprises any of: an intensity component, a location component, and a motion component.

3. The method of claim 2, wherein said video imaging device is a color video camera comprising red, green and blue channels and said intensity component is obtained from any of said channels.

4. The method of claim 2, wherein said video imaging device is a color video camera comprising red, green and blue channels and said intensity component is obtained from computing an algebraic sum of pixel values from said red, green and blue channels.

5. The method of claim 1, wherein, in advance of forming said feature vectors, grouping pixels associated with said features and computing their mean values.

6. The method of claim 5, further comprising spatial filtering said grouped pixels to reduce noise.

7. The method of claim 5, further comprising amplitude filtering by taking an L2 norm of each row vector and retaining all feature points with an L2 norm that is below a pre-defined maximum value.

8. The method of claim 1, wherein said video matrix comprises orthonormal eigenvectors obtained by computing mean and covariance matrices using singular value decomposition.

9. The method of claim 8, wherein, in advance of computing said mean and covariance matrices, computing a derivative of said video matrix.

10. The method of claim 1, wherein eigenvectors are computed by performing singular value decomposition on said video matrix.

11. The method of claim 10, wherein, in advance of performing singular value decomposition, computing a derivative of said video matrix.

12. The method of claim 1, wherein extracting said respiration rate from said selected eigenvector comprises:
   generating a power spectral density curve for said selected eigenvector; and
   identifying a frequency within said power spectral density curve with a highest signal strength, said identified frequency being said subject's respiration rate.

13. The method of claim 1, wherein extracting said respiration rate from said selected eigenvector comprises:
   computing peak to peak interval between adjacent peaks; and
   computing frequency from select group of peak to peak intervals.

14. The method of claim 1, wherein, in response to said subject's respiration rate not being within a normal range, performing any of: initiating an alert, and signaling a medical professional.

15. The method of claim 1, further comprising using said respiratory rate to facilitate a determination of an occurrence of any of: Sudden Infant Death Syndrome, Respiratory Distress, Respiratory Failure, and Pulmonary Disease.

16. The method of claim 1, wherein said video is a streaming video and said respiration rate is determined for said subject in real-time.

17. A system for determining respiration rate from a video of a subject being monitored for respiratory function, the system comprising:
   a video imaging device for capturing video comprising a plurality of time-sequential image frames of at least one region of interest of a subject's body where a signal corresponding to respiration can be registered by at least one imaging channel of said video imaging device;
   a processor in communication with a memory and executing machine readable instructions for performing:
     receiving said video of a subject;
     extracting, from said region of interest from said plurality of image frames, features of pixels and forming vectors of length N from said extracted features;
     constructing a N×M video matrix of temporally sequential feature vectors, a total number of columns M in said video matrix corresponding to a time duration over which a respiration rate for said subject is to be determined;
     processing said video matrix to obtain a matrix of eigenvectors, said eigenvector matrix being such that principal axes of variations due to motion associated with said subject's respiration are contained in a first few eigenvectors;

selecting one eigenvector from said first few eigenvectors; and extracting a respiration rate for said subject from said selected eigenvector.

18. The system of claim 17, wherein said feature vector comprises any of: an intensity component, a location component, and a motion component.

19. The system of claim 15, wherein said video imaging device is a color video camera comprising red, green and blue channels and said intensity component is obtained from any of said channels.

20. The system of claim 15, wherein said video imaging device is a color video camera comprising red, green and blue channels and said intensity component is obtained from computing an algebraic sum of pixel values from said red, green and blue channels.

21. The system of claim 20, wherein, in advance of forming said feature vectors, grouping pixels associated with said features and computing their mean values.

22. The system of claim 21, further comprising spatial filtering said grouped pixels to reduce noise.

23. The system of claim 21, further comprising amplitude filtering by taking an L2 norm of each row vector and retaining all feature points with an L2 norm that is below a pre-defined maximum value.

24. The system of claim 17, wherein said video matrix comprises orthonormal eigenvectors obtained by computing mean and covariance matrices using singular value decomposition.

25. The system of claim 24, wherein, in advance of computing said mean and covariance matrices, computing a derivative of said video matrix.

26. The system of claim 17, wherein eigenvectors are computed by performing singular value decomposition on said video matrix.

27. The system of claim 26, wherein, in advance of performing singular value decomposition, computing a derivative of said video matrix.

28. The system of claim 17, wherein extracting said respiration rate from said selected eigenvector comprises:
generating a power spectral density curve for said selected eigenvector; and
identifying a frequency within said power spectral density curve with a highest signal strength, said identified frequency being said subject's respiration rate.

29. The system of claim 17, wherein extracting said respiration rate from said selected eigenvector comprises:
computing peak to peak interval between adjacent peaks; and
computing frequency from select group of peak to peak intervals.

30. The system of claim 17, wherein, in response to said subject's respiration rate not being within a normal range, performing any of: initiating an alert, and signaling a medical professional.

31. The system of claim 17, further comprising using said respiratory rate to facilitate a determination of an occurrence of any of: Sudden Infant Death Syndrome, Respiratory Distress, Respiratory Failure, and Pulmonary Disease.

* * * * *